United States Patent [19]

Takahashi et al.

[11] Patent Number: 5,882,938

[45] Date of Patent: *Mar. 16, 1999

[54] APPARATUS AND METHOD FOR EVALUATING CONTAMINATION CAUSED BY ORGANIC SUBSTANCES DEPOSITED ON SUBSTRATE SURFACE

[75] Inventors: Hideto Takahashi; Soichiro Sakata; Katsumi Sato, all of Kanagawa-ken, Japan

[73] Assignee: Takasago Thermal Engineering Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 658,247

[22] Filed: Jun. 4, 1996

[30] Foreign Application Priority Data

Jun. 13, 1995 [JP] Japan ................................ 7-171373

[51] Int. Cl.$^6$ .......................... G01N 27/04; G01N 27/12
[52] U.S. Cl. .......................... 436/151; 436/149; 422/62; 422/82.02; 422/98; 134/1; 134/2
[58] Field of Search ....................... 436/151, 149; 134/1, 1.1, 1.2, 1.3, 2, 18, 757, 717, 754; 422/62, 82.01, 82.02, 83, 98

[56] References Cited

U.S. PATENT DOCUMENTS

| | | | |
|---|---|---|---|
| 3,628,137 | 12/1971 | Mazur | 324/717 |
| 3,644,829 | 2/1972 | Chan et al. | 324/757 |
| 3,676,775 | 7/1972 | Dupnock et al. | 324/717 |
| 3,890,564 | 6/1975 | Wanatabe et al. | 324/225 |
| 3,947,765 | 3/1976 | Diehl et al. | 324/756 |
| 5,260,668 | 11/1993 | Mallory et al. | 324/719 |
| 5,491,424 | 2/1996 | Asar et al. | 324/715 |
| 5,578,504 | 11/1996 | Mitani et al. | 437/8 |

FOREIGN PATENT DOCUMENTS

| | | |
|---|---|---|
| 0 365 342 | 4/1990 | European Pat. Off. . |
| 749010 | 12/1996 | European Pat. Off. . |
| 232410 | 1/1986 | Germany . |
| 3814662 | 12/1989 | Germany . |
| 4-31740 | 2/1992 | Japan . |
| 7-176580 | 7/1995 | Japan . |

OTHER PUBLICATIONS

Coles et al, CAS abstract 104:41855, 1985.

Allison et al, CAS abstract 121:159750, 1991.

Hideto Takahashi et al., Charge Leakage Characteristics of Glass Substrate for LCD, Prc. Inst. Electrostat Jpn., Apr. 18, 1994 (364–370).

Hideto Takahashi et al., Charge Leakage Characteristics of Glass Substrate for Liquid Crystal Display, Journal of Elctrostatics 35, 1995, (309–322).

*Primary Examiner*—Jill Warden
*Assistant Examiner*—Alexander Markoff
*Attorney, Agent, or Firm*—Patterson Belknap Webb & Tyler, LLP

[57] ABSTRACT

Apparatus and a method for evaluating the contamination over the surface of a substrate for use in manufacturing semiconductor devices, liquid crystal devices and so on, said contamination being caused by contaminants, for instance airborne organic substances or the equivalent in the clean room atmosphere. For evaluation, there is measured with passage of time in the atmosphere having a substantially constant relative humidity the surface resistivity (R) of the substrate 104 by bringing electrodes 106 into close contact with an insulating film as formed on said substrate surface, or a contact angle (α) of a liquid-drop 207 dropped on the substrate 206. From this measurement, the degree of said contamination is judged by comparing the value of the surface resistivity or contact angle as measured immediately after rinsing the substrate, with the values of the same as measured after exposing the substrate to the objective atmosphere to be evaluated.

9 Claims, 11 Drawing Sheets

APPARATUS AND METHOD FOR EVALUATING CONTAMINATION CAUSED BY ORGANIC SUBSTANCES DEPOSITED ON SUBSTRATE SURFACE

BACKGROUND OF THE INVENTION

1. Field of the Invention

The present invention relates to apparatus and a method for evaluating contamination over a substrate surface which is caused by organic substances deposited on thereon, said substrate being used for manufacturing semiconductor devices, liquid crystal displays (LCD), and so forth. More particularly, the invention relates to apparatus and a method for evaluating contamination caused by the organic substances that are contained in the atmosphere of a clean room for manufacturing semiconductor devices, LCDs, and so forth, and are deposited on the surface of the semiconductor substrate, the glass substrate, or the like others.

In the following description, the contamination of this kind is called 'atmosphere originated organic contamination' for simplification. Also, in the following description, unless noted otherwise specially, an expression 'a substrate' or 'the substrate' represents the semiconductor substrate, the glass substrate, or the like others.

2. Description of the Related Art

In the clean room for manufacturing semiconductor devices, LCDs, and other sophisticated products, if organic substances contained in the clean room atmosphere adhere to the insulating film surface that is formed on the semiconductor substrate, the glass substrate, or the like others, they exert a bad influence on the electric characteristics of the semiconductor device and LCD, for instance causing increase of the leakage current and decrease of the breakdown voltage. It might be true that these organic substances deposited on the substrate surface can be readily removed by various rinsing techniques, for instance by the ultraviolet rays/ozone rinsing method. However, since several minutes have to be spent for rinsing one substrate, should it be needed to carry out such rinsing so often, the throughput of the production would be naturally reduced. Therefore, it is desirous to develop a simple method for quantitatively evaluating the atmosphere originated organic contamination. If such a evaluation method is developed and applied to the manufacturing process of semiconductor devices and LCDs, it will become possible to decompose and remove the organic substances deposited on the substrate surface by timely rinsing of the substrate before the atmosphere originated organic contamination reaches such a level that causes deterioration of their electric characteristics. Furthermore, it will become also possible to reduce the number of the steps of rinsing the substrate by carrying out it only when judged necessary in view of the contamination level as evaluated.

It has been known that for evaluating the clean room atmosphere originated organic contamination over the semiconductor substrate and the glass substrate, the quantity of the organic substances deposited on the substrate surface is measured by using the method of X-ray photoelectron spectroscopy (referred to as XPS method hereinafter). In this XPS method, a substrate for use in sampling the contaminants (referred to as the sampling substrate hereinafter) is irradiated with the soft X-rays in the high vacuum circumstances, and the energy and the number of photoelectrons expelled out from said sampling substrate by this X-ray irradiation are measured by the spectrometer, thereby carrying out the qualitative/quantitative analysis of the elements existing on the sampling substrate surface. In the evaluation of the minute atmosphere originated organic contamination quantity over the substrate surface by the XPS method, the evaluation result is expressed as a ratio of the number of carbon atoms to the number of all the atoms existing within the objective region to be analyzed which extends to the depth of several tens angstroms(Å) from the surface, or as a ratio of the number of carbon atoms to the atom number of the known elements existing in said objective region.

Since the atmosphere originated organic contamination quantity can be measured with high precision by the XPS method, this method might be regarded as an effective means for evaluating the atmosphere that causes the atmosphere originated organic contamination over the semiconductor substrate and the glass substrate. However, this method indispensably requires a higher vacuum system and a spectrometer, so that it would highly cost as a whole.

Briefly explaining the analysis by the XPS method, a sampling substrate with a clean surface is first prepared, and then, it is exposed to the objective atmosphere to be evaluated for a predetermined period of time. After this, the sampling substrate has to be transferred to an analyzing room for analysis by an analyzer. Accordingly, in the XPS method, sampling of the contaminants and analysis thereof have to be carried out at separate places. In other words, the analysis by the XPS method can not but be a so-called off-line analysis. Especially, if the XPS apparatus is located at a distance from the sampling point, there can be considered the possibility that the surface of the sampling substrate might be contaminated while it is transferred. Namely, the XPS method must be excellent for the R&D purpose. However, in the actual manufacturing process of semiconductor devices and LCDs, the atmosphere originated organic contamination has to be continuously monitored under the condition that the sampling by the sampling substrate and the analysis thereof can be carried out at an identical place. Therefore, it would be said that the XPS method is not so suitable for the purpose of a so-called in-line analysis.

SUMMARY OF THE INVENTION

Accordingly, an object of the present invention is to provide a novel and improved apparatus and a method for simply and economically evaluating the atmosphere originated organic contamination over the surface of the semiconductor substrate, the glass substrate, and the like others.

Further, another object of the invention is to provide a novel and improved apparatus and a method which are capable of judging the degree of the atmosphere originated organic contamination over the substrate surface at the actual site of manufacturing semiconductor substrates, glass substrates, and the like others, and are suitable for the in-line analysis of said organic contamination.

Still further, another object of the invention is to reduce the number of the steps of rinsing the substrate unnecessarily, thereby increasing the throughput of the manufacturing process, and at the same time, to increase the yield of manufacturing by rinsing the substrate and/or removing the organic substances contained in the atmosphere in correspondence with necessity thereof.

According to a first aspect of the invention, there is provided apparatus for evaluating the atmosphere originated organic contamination over the substrate surface. This evaluation apparatus comprises a substrate of which at least the surface is dielectric; a surface resistivity measuring device for measuring the electric resistance between at least two points on said substrate surface; an isolated space for accommodating said substrate; means for introducing a humidity regulated gas (for instance, inert gas and/or purified air) into said isolated space, said humidity regulated gas having a substantially constant relative humidity in said isolated space; means for introducing the objective gas to be evaluated into said isolated space; and means for evaluating the atmosphere originated organic contamination over the substrate surface in correspondence with the surface resistivity as measured by said surface resistivity measuring device.

The surface resistivity measuring device as adopted by this evaluation apparatus may be constituted to have a plurality of conductive electrodes which are formed so as to closely get in contact with the insulating surface of said substrate. Also, the surface resistivity measuring device may be constituted to have a plurality of conductive electrodes which are movably formed so as to move back and forth against the insulating surface of said substrate.

Furthermore, said evaluation apparatus may be provided with means for generating ultraviolet rays by which said substrate accommodated in said isolated space can be irradiated, and also with means for introducing a cleaning gas into said isolated space, said cleaning gas containing at least oxygen.

According to a second aspect of the invention, there is provided a method of evaluating the atmosphere originated organic contamination over the substrate surface. This evaluation method comprises the steps of introducing a humidity regulated gas (for instance, inert gas/purified gas) having a predetermined relative humidity, into an isolated space accommodating a substrate of which at least the surface is dielectric, and measuring the surface resistivity between at least two points on said substrate surface; introducing the objective gas to be evaluated into said isolated space, and exposing said substrate to said objective gas for a predetermined period of time; introducing a humidity regulated gas having the substantially same relative humidity as said predetermined relative humidity into said isolated space, and measuring the surface resistivity between at least two points on said substrate surface having been exposed to the objective gas; and evaluating the atmosphere originated organic contamination over the substrate surface in correspondence with the change in the surface resistivity as measured.

Also, the method as described above may be constituted by adding the steps of introducing into said isolated space a cleaning gas containing at least oxygen after finishing evaluation of the atmosphere originated organic contamination, and irradiating said substrate surface with ultraviolet rays. Further, in the method, it may possible to perform the steps of purging the gas having existed in said isolated space during the preceding step before introducing the gas for the following step into said isolated space.

The operation of the apparatus and method as constituted according to the first and second aspects of the invention will be described in the following.

A substrate of which the surface is dielectric (for instance, formed of the insulating film, the ceramics, or the like) is set up in the isolated space. In this case, the organic substances have to be removed from the substrate surface in advance. Next, by the means for introducing the humidity regulated gas, the humidity regulated gas (for instance, inert gas and/or purified air), of which the relative humidity is kept at a predetermined value, is introduced to the isolated space, thereby the relative humidity in the isolated space being controlled to have said predetermined value.

Then, a surface resistivity (Rsi) between at least two points on said substrate surface is measured by the surface resistivity measuring device. In this case, if the electrode portion of said measuring device is formed of a plurality of electrodes closely getting in contact with the insulating surface of the substrate, a measuring voltage is directly applied to those electrodes, thereby measuring the surface resistivity (Rsi) of the substrate surface immediately after removing the organic substances therefrom. In contrast to this, if the electrode portion of said measuring device is formed of a plurality of electrodes which can move back and forth against the dielectric surface of the substrate, a measuring voltage is applied to those electrodes after bringing them into close contact with said dielectric surface, thereby measuring the surface resistivity (Rsi) of the substrate surface immediately after removing the organic substances therefrom.

After measurement of this surface resistivity (Rsi), the objective gas to be evaluated is introduced into said isolated space by the means for introducing the objective gas. For introduction of the objective gas, two ways are available: one is to compulsively supply the objective gas to the isolated space by such a gas supply means as an air pump, and the other is to naturally fill up the isolated space with the objective gas by opening an openable door in the atmosphere containing the objective gas, said door being arranged on the partition wall for separating the isolated space from said atmosphere.

After exposing said substrate to said objective gas for a predetermined period of time, the isolated space is separated from the surrounding space, and the humidity regulated gas (for instance, inert gas and/or purified air) having the substantially same relative humidity as said predetermined relative humidity is again introduced into said isolated space by the means for introducing the humidity regulated gas, thereby controlling the relative humidity in the isolated space to make it substantially same as said predetermined value. Then, the surface resistivity (Rsf) is measured in the same manner as has been done previously. As the inventors of the present invention is discussing in connection with FIG. 2 in their paper entitled 'Charge Leakage Characteristics of Glass Substrate for LCD' (The Institute of Electrostatics Japan, Vol. 18, No. 4, 1994, pp 364–370), the surface resistivity of the glass substrate contaminated with a certain quantity of organic substances largely depends on the relative humidity of the atmosphere to which the substrate is exposed during the measurement of its surface resistivity. Therefore, in case of putting the present invention into practice, it should be noted that the relative humidity of the humidity regulated gas which is used for measuring the surface resistivity (Rsf) of the substrate after exposure to the objective atmosphere, should be controlled to be substantially identical to that of the humidity regulated gas as used for measuring the surface resistivity (Rsi) of the substrate immediately after rinsing the substrate.

In this way, the degree of the atmosphere originated organic contamination over the semiconductor substrate and the glass substrate can be obtained by the evaluation means as a ratio of the surface resistivity (Rsf) of the substrate as measured after exposure to the objective gas to the surface resistivity (Rsi) of the substrate as measured immediately after rinsing the substrate. Further, if the measurement of the surface resistivity (Rsf) is repeated, it can be known how the surface resistivity (Rsf) caused by the atmosphere originated organic contamination changes with passage of time. Accordingly, in this way, a period of time until the degree of atmosphere originated organic contamination exceeds a certain limit, in other words, the maximum allowable exposure time, can be known by measuring how much the surface resistivity as measured after exposure to the clean room atmosphere for a certain constant time is increased from that which has been measured immediately after rinsing the substrate.

After finishing a series of measurements of the change with passage of time regarding the surface resistivity, the electrodes may be left as they are, if the electrode portion of the surface resistivity measuring device is formed of a plurality of electrodes closely getting in contact with the insulating surface of the substrate. In contrast to this, if the electrode portion of said measuring device is formed of a plurality of electrodes which can move back and forth against the dielectric surface of the substrate, the electrode portion is lifted up to separate it from the insulating surface of the substrate. After this, the cleaning gas containing at least oxygen is introduced into the isolated space by the means for introducing the cleaning gas, and at the same time, the ultraviolet ray generating means like the ultraviolet lamp irradiates the substrate surface in order to perform the ultraviolet/ozone cleaning for decomposing and removing the organic substances deposited on the substrate surface. The ozone gas generated in the isolated space during said irradiation is properly exhausted, and the evaluation apparatus comes to be on standby for performing the next measurement of the change with passage of time as for the surface resistivity.

According to the third aspect of the present invention, there is provided apparatus for evaluating the atmosphere originated organic contamination over the surface substrate. This apparatus comprises a substrate; means for dropping a liquid-drop on the surface of the substrate (preferably, capable of dropping a liquid-drop on the desired point on the substrate surface); means for measuring the contact angle of said dropped liquid-drop (for instance, consisting of a light source for lighting the dropped liquid-drop and means for observing said dropped liquid-drop by optically magnifying the image of it); an isolated space for accommodating said substrate; means for introducing the objective gas to be evaluated into said isolated space; and means for evaluating the atmosphere originated organic contamination over the substrate surface in correspondence with the contact angle as measured.

Also, it is preferable that the means for dropping liquid-drop and/or the substrate can be constituted to relatively move to each other, thereby enabling the liquid-drop to be dropped to a desired dropping point on the substrate surface. Further, in the above evaluation apparatus, there may be provided means for generating ultraviolet rays which is accommodated in the isolated space and is for irradiating the substrate surface and means for introducing a cleaning gas containing at least oxygen into said isolated space.

According to the fourth aspect of the present invention, there is provided a method for evaluating the atmosphere originated organic contamination. This method comprising the steps of dropping a liquid-drop to at least one dropping point on the surface of the substrate accommodated in said isolated space, and measuring the contact angle of the dropped liquid-drop; introducing the objective gas to be evaluated into said isolated space, and exposing said substrate to said objective gas for a predetermined period of time; dropping another liquid-drop to at least another dropping point, which is different from said previous dropping point, on the substrate surface exposed to the objective gas, and then, measuring the contact angle thereof; and evaluating the atmosphere originated organic contamination over the substrate surface in correspondence with the change of the contact angle as measured.

Also, the above evaluation method may additionally include the steps of introducing into said isolated space a cleaning gas containing at least oxygen after completing evaluation of the atmosphere originated organic contamination, and irradiating said substrate surface with ultraviolet rays. Further, the above evaluation method may include the step of purging the gas having existed in said isolated space during the preceding step, before introducing the gas for the following step into said isolated space.

The operation of the apparatus and method as constituted according to the third and fourth aspects of the invention will be described in the following.

As shown in FIG. 9, the apparatus and method as constituted based on the third and fourth aspects of the invention make use of the phenomenon that when an ultra-pure waterdrop is dropped on the substrate surface, the contact angle ($\alpha$) of the waterdrop increases in response to the increase of the quantity of organic contaminants over the substrate surface. Namely, the silicon wafer surface covered by an oxide film and the glass substrate surface, which are free from contamination caused by the organic substances, are hydrophilic so that the contact angle thereof becomes smaller. Contrary to this, if they are contaminated with organic substances, they becomes hydrophobic so that the contact angle thereof becomes larger. Since this contact angle can be readily measured by optically magnifying the image of the waterdrop illuminated by the light source, the evaluation of contamination over the substrate surface can be simply carried out at a lower cost in comparison with the evaluation by the XPS method.

In case of performing the evaluation, the substrate is set up inside the isolated space. In this case, the organic substances have to be removed from the substrate surface in advance. Next, a liquid-drop (for instance, ultra-pure waterdrop) is dropped on the substrate surface by the means of dropping the liquid-drop, which is for instance, a syringe arranged above the substrate. Then, the liquid-drop as dropped on the substrate surface is illuminated by the light source, and the contact angle of the liquid-drop on the substrate surface immediately after being rinsed is measured through the image of the liquid-drop magnified by a magnifying glass.

After measuring the contact angle, the objective gas to be evaluated is introduced into said isolated space by the means for introducing the objective gas. In case of introducing the objective gas, two ways are available as previously described. Namely, one is to compulsively supply the objective gas to the isolated space by a gas supply means like an air pump, and the other is to naturally fill up the isolated space with the objective gas by opening an openable door in the atmosphere containing the objective gas, said door being arranged on the partition wall for separating the isolated space from the surrounding atmosphere.

After exposing said substrate to said objective gas for a predetermined period of time, the isolated space is isolated from the circumferential atmosphere, and the substrate and/or the means for dropping the liquid-drop is relatively moved to each other in a horizontal plane, thereby dropping another liquid-drop on another dropping point of the substrate surface that is different from the point on which the preceding liquid-drops already exist. Next, the liquid-drop dropped on the substrate surface is illuminated by the light source, and the image of the liquid-drop in the light is observed by the magnifying glass, thereby measuring the contact angle of the liquid-drop after exposure to the objective gas for a predetermined period of time.

In this way, the degree of the atmosphere originated organic contamination over the semiconductor substrate and the glass substrate can be obtained by the evaluation means as a change rate of the contact angle of the dropped liquid-drop as measured after exposure to the objective gas to the contact angle of the dropped liquid-drop as measured immediately after rinsing the substrate. Further, if the measurement of the contact angle is repeated, it can be known how the contact angle changes with passage of time by the atmosphere originated organic contamination. Further, a period of time until the degree of atmosphere originated organic contamination exceeds a certain limit, namely the maximum allowable exposure time, can be known by measuring how much the contact angle after exposure to the clean room atmosphere for a certain constant time is increased from the contact angle as measured immediately after rinsing the substrate.

After finishing a series of measurements of the change with passage of time as to the contact angle, the cleaning gas containing at least oxygen is introduced into the isolated space by the means for introducing the cleaning gas, and at the same time, the ultraviolet ray generating means like the ultraviolet lamp irradiates the substrate surface in order to carry out the ultraviolet/ozone cleaning for decomposition and removal of the organic substances on the substrate. The ozone gas generated in the isolated space during the cleaning is properly exhausted, and the evaluation apparatus comes to stand ready for performing the next measurement of the change with passage regarding the contact angle.

DETAILED DESCRIPTION OF THE PREFERRED EMBODIMENT

In reference with the accompanying drawings, the invention will now be described in detail in the following, in connection with several exemplary embodiments of the apparatus and method for evaluating the atmosphere originated organic contamination over the substrate surface, which are constituted according to the present invention.

First Embodiment

Figure 1:
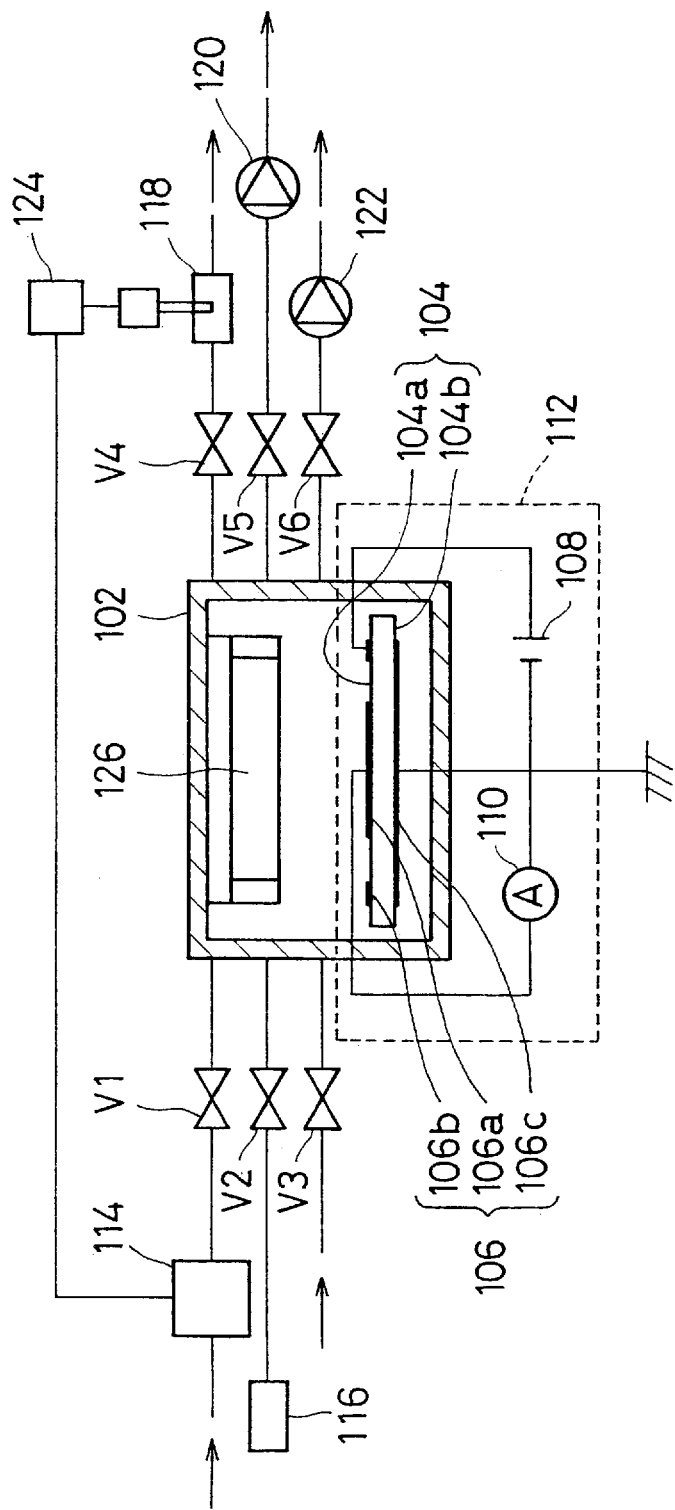
FIG. 1 is a schematic diagram showing the apparatus for evaluating the atmosphere originated organic contamination over the substrate surface according to the first preferred embodiment of the present invention.
Figure 2B:
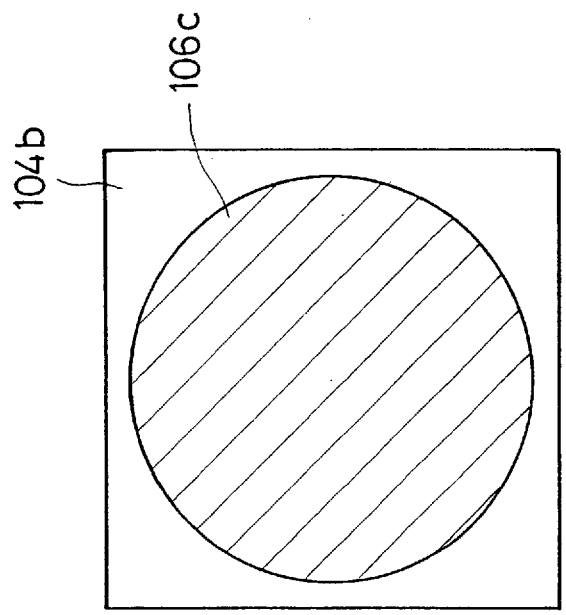
FIG. 2(B) is a plan view showing the constitution of electrodes which are formed on the back of the substrate and made applicable to the first and second embodiments according to the invention.
Figure 2A:
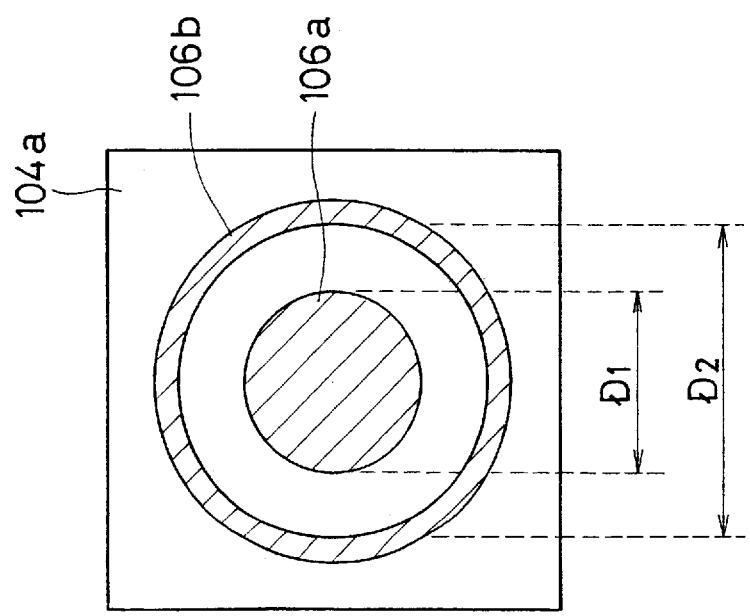
FIG. 2(A) is a plan view showing the constitution of electrodes which are formed on the front surface of the substrate and made applicable to the first and second embodiments according to the invention.

First, the invention will be described in detail in connection with the first embodiment thereof. FIG. 1 is a schematic constitutional view showing apparatus for evaluating the atmosphere originated organic contamination over the substrate surface according to the first embodiment of the invention. As shown in the figure, the apparatus is provided with an isolated space 102 isolated from the outside. This isolated space 102 may be constituted as a chamber that is isolated from the outside by means of partitions made of such a material as aluminum, for instance. In this isolated space 102, there is set up a glass substrate 104 (CORNING #7059, 100×100 mm$^2$×1.1 mm$^r$) having a clean surface 104$a$ from which organic substances have been removed. The glass substrate 104 has a plurality of metal electrodes 106 for use in measuring the surface resistivity, which are formed on both front and back surfaces of the glass substrate by evaporation. FIGS. 2(A) and 2(B) are schematic views showing the metal electrodes 106 formed on the glass substrate 104 by evaporation. As shown in the figures, the metal electrodes 106 comprises a first electrode 106$a$ which is formed, by evaporation, on the surface 104$a$ of the glass substrate 104, having an almost circular shape placing its center at about the center of said surface 104$a$, a second electrode 106$b$ which is prepared in the annular form coaxially surrounding the first electrode 106$a$, and a grounding electrode 106$c$ which is formed, by evaporation, on the back surface 104$b$ of the glass substrate 104, having an almost circular shape. These electrodes 106 may be formed by directly depositing, by evaporation, a conductive material on the front and back surfaces 104a, 104b of the glass substrate 104. Also, these electrodes 106 may be formed by first forming an insulating film over both front and back surface 104a, 104b of the glass substrate 104, for instance by using the plasma CVD method, and then depositing the conductive material on the insulating film by using a sputtering apparatus. Furthermore, between the first and second electrodes 106a, 106b, there are connected in series a power source 108 and an ammeter 110 as well, thereby a surface resistivity measuring device 112 (a rectangular part surrounded by a dotted line in FIG. 1) being constituted. In FIG. 1, the surface resistivity measuring device is illustrated as if it had to be constituted including the substrate 104 and a part of the isolated space 102, but it should be noted that this has been done just for readers' easy understanding the constitution of the present embodiment. Accordingly, the surface resistivity measuring device 112 is not limited to the described hereinabove, but may be of any type that can measure the electrical resistivity at least between two points on the surface of the sampling substrate 104. It should be also noted that the glass substrate is being used as the sampling substrate 104 in the present embodiment, but it is possible to use the other substrate as the sampling substrate in correspondence with an objective matter to be measured. For instance, a silicon wafer on which an insulating layer is formed, may be used as the sampling substrate if electrodes 106 are arranged on its surface so as to constitute the surface resistivity measuring device 112.

Further, the isolated space 102 is constituted in such a manner that the pressurized and purified air having the humidity regulated by a humidifier 114 can be introduced therein through a gas supply valve V1, that the oxygen gas can be introduced therein through a gas supply valve V2 from an oxygen cylinder 116, and further, that the objective atmosphere to be evaluated can be introduced through a gas supply valve V3. Still further, the isolated space 102 is connected with an exhaust valve V4 communicating with a humidity sensor 118, another exhaust valve V5 communicating with an exhaust pump 120, and still another exhaust valve V6 communicating with an air pump 122, respectively. The information on the relative humidity detected by the humidity sensor 118 is transmitted to a controller 124 which in turn performs the feedback control of the humidifier 114 in correspondence with the value of the relative humidity as detected by said humidity sensor. In the upper potion of the isolated space 102, there is disposed an ultraviolet lamp 126 which emits ultraviolet rays to irradiate the surface 104a of the glass substrate 104.

In order to measure the surface resistivity of the glass substrate immediately after rinsing it, valves V2, V5, V3, and V6 are closed while valves V1 and V4 are opened, and the pressurized humidity regulated gas which is controlled to have a predetermined relative humidity, is introduced into the isolated space 102. The pressurized humidity regulated gas can be produced by using a so-called flow distribution method i.e. by supplying the pressurized and purified air to the humidifier 114. The flow quantity distributed to the humidifier 114 is feedback controlled with the help of the humidity sensor 118 and the controller 124 which are disposed at the outlet side of the humidity regulated gas, so as to maintain the relative humidity in the isolated space 102 at a predetermined constant level. After the relative humidity in the isolated space 102 has reached a predetermined level, the voltage is applied to the electrode 106 for measuring the surface resistivity, thereby the initial surface resistivity (Rsi) of the clean glass substrate being measured by the surface resistivity measuring device 112.

Since the surface resistivity of the substrate can be defined as the resistance per unit area, this is equivalent to the resistance per square meter of the material. Accordingly, the surface resistivity (Rs) can be calculated from the following expression (1).

$$Rs = \frac{c}{d} R \qquad (1)$$

where
RS : surface resistivity ($\Omega$)
c : circumferential length (mm)
d : gap (mm)
R : sheet resistivity as measured by the surface resistivity measuring device ($\Omega$)

When using the dimension of the electrodes as shown in FIG. 2(A), the expression (1) can be rewritten as the following expression (2).

$$Rs = \frac{\pi(D_1 + D_2)}{D_2 - D_1} R \qquad (2)$$

where
$D_1$ : outer diameter of electrode 106a (mm)
$D_2$ : inner diameter of electrode 106b (mm)

Next, the objective atmosphere to be evaluated is sucked in the isolated space 102 by closing valves V1, V4, opening valves V3, V6, and operating the air pump 122. Then, the surface 104a of the glass substrate 104 is exposed to said objective atmosphere for a predetermined period of time. After completing the exposure of the substrate surface, valves V3, V6 are closed while valves V1, V4 are opened. Then, the controller 124 operates to return the relative humidity in the isolated space 102 to a predetermined relative humidity (substantially equal to the relative humidity at which the surface resistivity of the substrate was measured immediately after rinsing it). Then, the surface resistivity (Rs) of the substrate surface is measured by the surface resistivity measuring device 112. Accordingly, if the measurement of the surface resistivity (Rsf) is repeated at regular intervals in the way as described above, it is possible to pursue or monitor the change with passage of time in respect of the quantity of organic contaminants on the clean substrate surface.

As described hereinbefore, the isolated space 102 is provided with the ultraviolet (UV) lamp 126. After a series of measurements of the change with passage of time in respect of the surface resistivity are finished, valves V1, V4, V3, and V6 are closed while valves V2 and V5 are opened in order to supply the pressurized oxygen gas from the oxygen cylinder 116 to the isolated space 102. At the same time, the surface 104a of the substrate 104 is irradiated with UV rays from the UV lamp, thereby the organic contaminants deposited on the surface 104a being decomposed and removed by the so-called UV rays/ozone cleaning. After this UV rays/ozone cleaning, the valve V2 is closed while the valve V1 is opened keeping the valve V5 opened. Then, the exhaust pump 120 is driven to replace the gas in the isolated space 102 with the purified air, exhausting the ozone gas generated in the isolated space 102 during the UV rays/ozone cleaning. In this way, the evaluation apparatus comes to be on standby for measuring the change with passage of time in respect of the surface resistivity of the next clean glass substrate.

Figure 3:
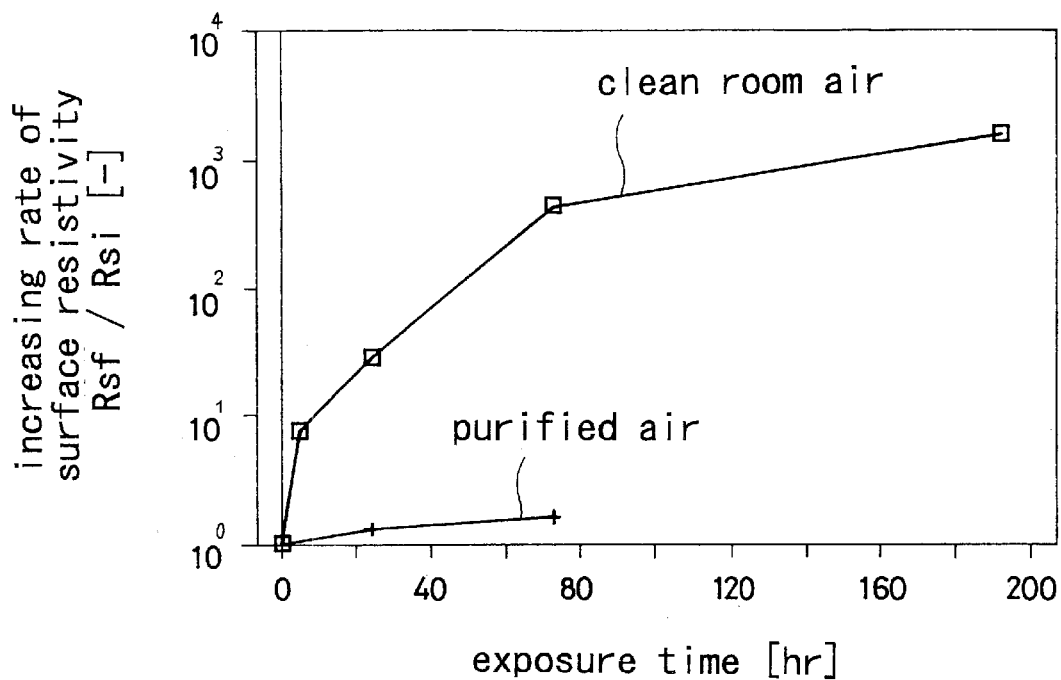
FIG. 3 is a graph showing the relation of the increasing rate of surface resistivity to the time of exposing the glass substrate surface to the specific atmosphere.

FIG. 3 is a graph showing the relation between increasing rate of the surface resistivity (Rsf/Rsi) and the exposure time of the substrate to the objective atmosphere, the graph being prepared based on results of the surface resistivity measurement of the glass substrate according to the abovementioned measuring steps, using the clean room air and the purified air (the air resulting from removing the organic contaminants from the clean room air) as the objective atmosphere to be evaluated. During this measurement, the relative humidity of the isolated space was maintained at 40%. As shown in this figure, in case of exposing the glass substrate to the clean room air, it is observed that its surface resistivity increases with passage of exposure time. Contrary to this, however, in case of exposing the same to the purified air, it is observed that its surface resistivity is hardly increased to the exposure time.

Figure 4:
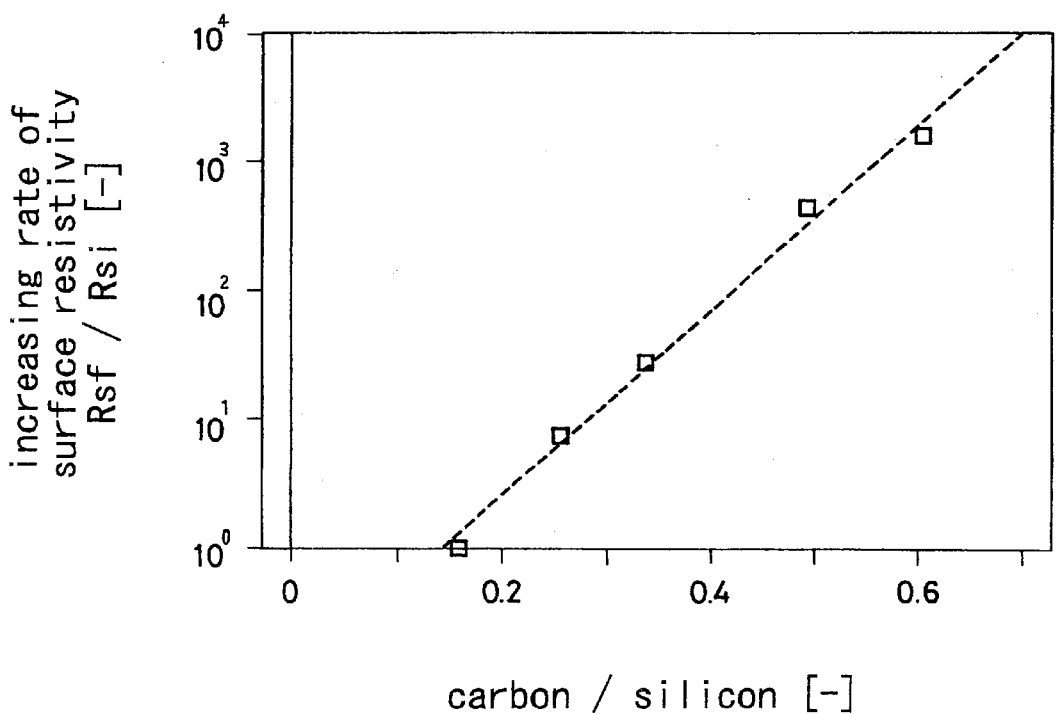
FIG. 4 is a graph showing the relation of the increasing rate of surface resistivity to the quantity of organic substances (ratio of carbon/silicon) adhered to the glass substrate surface.

FIG. 4 is a graph showing the relation between increasing rate of the surface resistivity (Rsf/Rsi) and quantity of organic contaminants (carbon/silicon) deposited on the substrate surface, the graph being prepared based on the measurement of the quantity of organic contaminants deposited on the surface 104a of the substrate 104 by the XPS method. In this case, the relative humidity of the isolated space is maintained 40% during the measurement of the surface resistivity. As shown in this figure, the surface resistivity increases corresponding to the increase in the quantity of organic contaminants. Accordingly, if this relation is made use of, it becomes possible to convert the measured value of the increasing rate of the surface resistivity into the quantity of the organic contaminants deposited on the glass substrate surface. For instance, if the glass substrate is exposed one by one to different various objective atmospheres for a predetermined period of time, and then the increasing rate of the surface resistivity is measured, it can be known from the results of respective measurements how much they contribute to contamination of the substrate surface as the sources thereof. Also, if the identical glass substrate is kept in a specific atmosphere and its surface resistivity is repeatedly measured at regular intervals, it can be monitored whether the atmosphere originated organic contamination against the glass substrate surface is below the allowable level or not.

Second Embodiment

Figure 5:
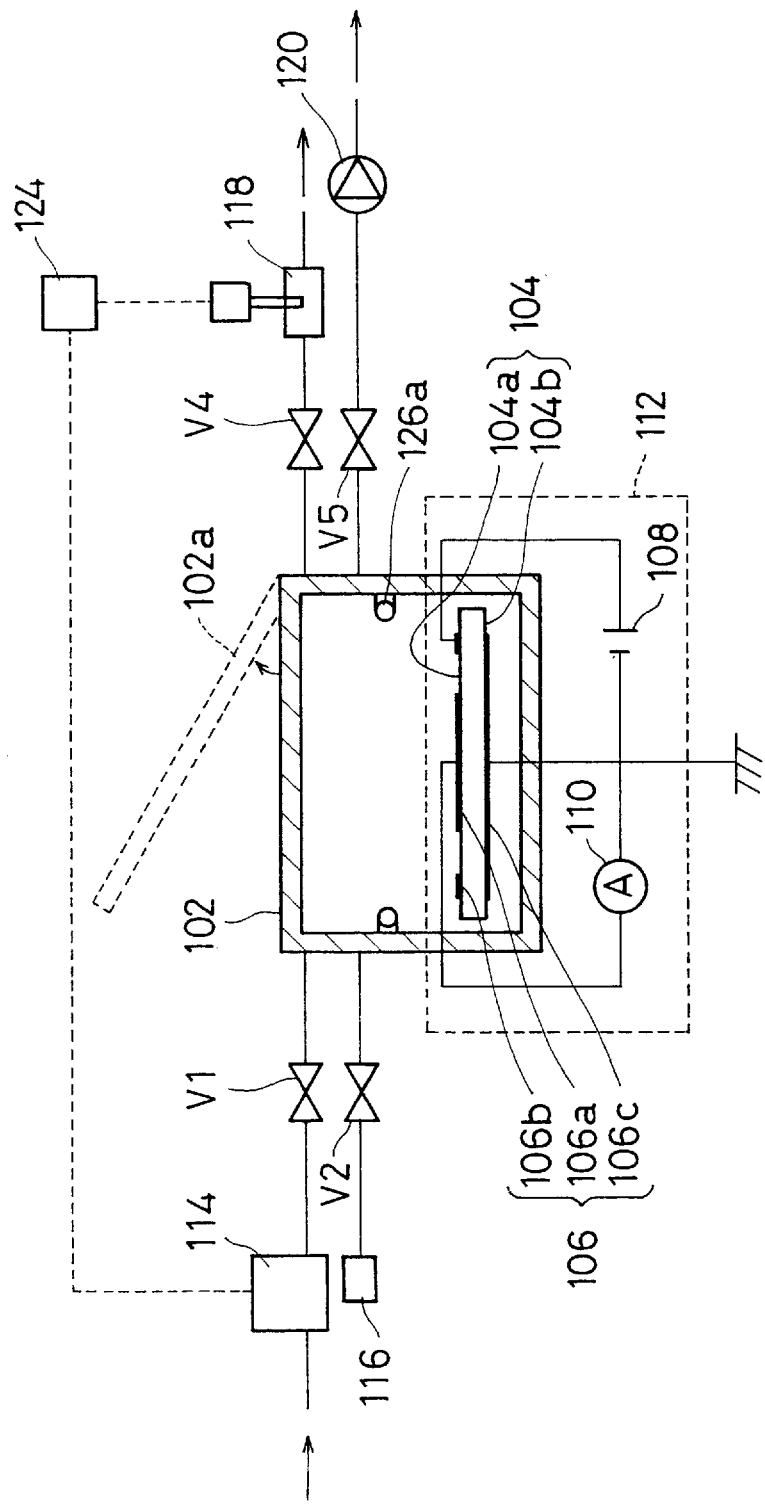
FIG. 5 is a schematic diagram showing the apparatus for evaluating the atmosphere originated organic contamination over the substrate surface according to the second preferred embodiment of the present invention.

The second embodiment of the invention will now be described in detail in the following. FIG. 5 is a schematic constitutional view showing the apparatus for evaluating the atmosphere originated organic contamination over the substrate surface. Regarding the constituents of the second embodiment shown in FIG. 5, which perform the substantially same functions as those of the first embodiment shown in FIG. 1, like reference numerals are assigned thereto, and no explanation thereabout will be made for avoiding redundant repetition thereof.

The second embodiment is different from the first embodiment shown in FIG. 1 in the following point. Namely, the different point is that one of partitions separating the isolated space 102 from the space surrounding thereof is provided with an openable door 102a, so that the atmosphere of said space can naturally flow in the isolated space 102 to fill it up therewith when the door 102a is opened. In connection with provision of this door 102a, valves V3, V6 and the exhaust pump 122 are eliminated, and the UV lamp 126a is disposed on the side portion of the isolated space so that the UV lamp does not disturb the opening and shutting movement of the door 102a. In the first embodiment, since the objective atmosphere to be evaluated can be compulsively supplied to the isolated space 102, the objective atmosphere to be evaluated may be located remote from the site where the isolated space 102 stands. For instance, the air in the storage room or chamber of materials to be kept clean, for instance silicon wafers and LCD glass substrates, can be introduced into the isolated space if there is provided the piping connecting therebetween. Contrary to this, according to the second embodiment, the objective atmosphere to be evaluated has to be the atmosphere surrounding the isolated space. For instance, this corresponds to the case where the objective atmosphere is the clean room atmosphere surrounding the isolated space.

Next, it is explained how the atmosphere originated organic contamination is evaluated according to the second embodiment.

First, there is provided an isolated space 102 separated from the atmosphere surrounding thereof, and a glass substrate 104 having the surface 104a which is made free from the organic substances by rinsing the substrate, is disposed in the isolated space 102. Then, valves V1, V4 are opened keeping valves V2, V5 closed, and the pressurized humidity regulated gas, of which the relative humidity is controlled to be a predetermined value by a humidifier 114, is introduced into the isolated space 102 through said humidifier. After the relative humidity in the isolated space 102 has reached said predetermined value, the voltage is applied to the electrode 106 for measuring the surface resistivity, and the initial surface resistivity (Rsi) of the clean glass substrate is measured by a surface resistivity measuring device 112.

Next, valves V1, V4 are closed while the door 102a is opened to fill up the isolated space 102 with the objective atmosphere to be evaluated, thereby exposing the surface 104a of the glass substrate 104 to the objective atmosphere for a predetermined period of time. Immediately after completion of this exposure process, the door 102a is closed. Then, valves V1, V4 are opened for recovering said predetermined relative humidity of the isolated space 102 (substantially equal to the relative humidity at which the surface resistivity of the substrate was measured immediately after rinsing it). After recovery of said relative humidity, the surface resistivity (Rsf) is measured. In this manner, in the same way as has been done in connection with the first embodiment, the change with passage of time in respect of the quantity of organic contaminants deposited on the clean substrate surface 104a can be pursued or monitored by repeating the measurement of the surface resistivity (Rsf) at regular intervals. The isolated space 102 is also provided with the UV lamp 126a as in the case of the first embodiment. After completing a series of measurements of the change with passage of time in respect of the surface resistivity, valves V1, V4 and the door 102a are closed while valves V2, V5 are opened, and then, the pressurized oxygen gas is supplied to the isolated space 102 from an oxygen cylinder 116. At the same time, the surface 104a of the substrate 104 is irradiated with UV rays, thereby the organic contaminants deposited on the surface 104a being decomposed and removed by means of the so-called UV rays/ozone cleaning. At this time, in the same manner as in the case of the first embodiment, the ozone gas generated in the isolated space 102 is exhausted by an exhaust pump 120. In this way, the evaluation apparatus comes to be in the standby position for measurement of the change with passage of time in respect of the surface resistivity of the next clean glass substrate.

Third Embodiment

Figure 6:
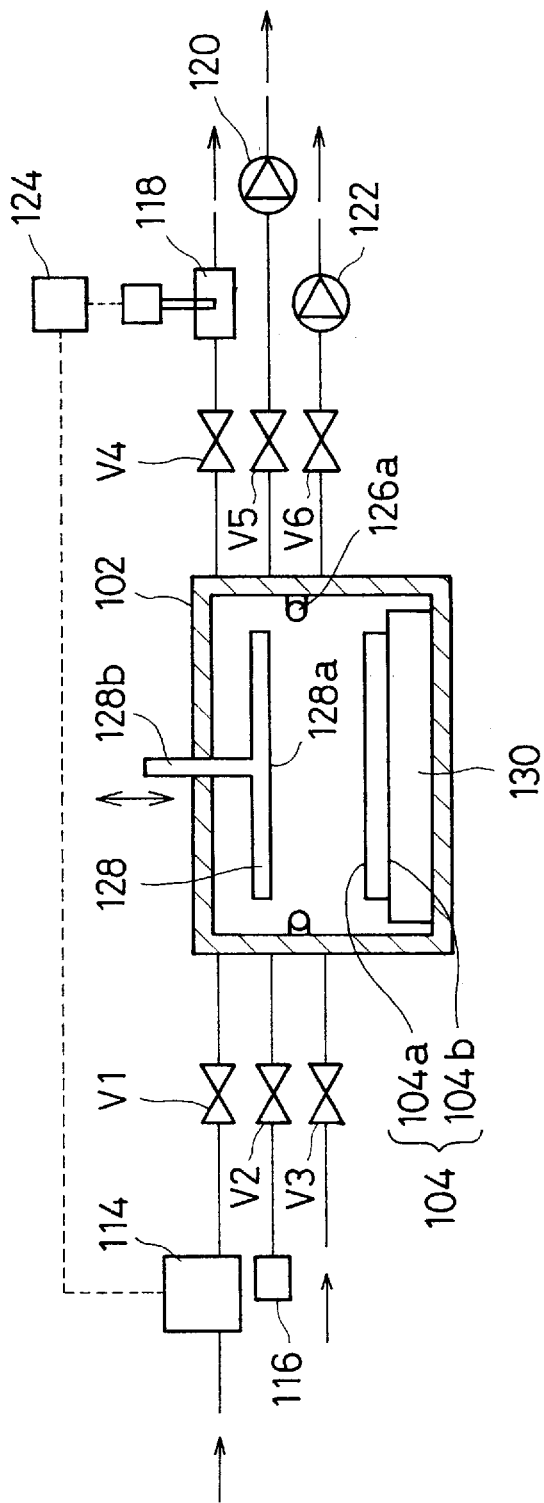
FIG. 6 is a schematic diagram showing the apparatus for evaluating the atmosphere originated organic contamination over the substrate surface according to the third preferred embodiment of the present invention.

The third embodiment of the present invention will now be described in detail in the following. FIG. 6 is a schematic constitutional view showing the apparatus for evaluating the atmosphere originated organic contamination. As to the constituents of the third embodiment shown in FIG. 6, which perform the substantially same functions as those of the first and second embodiments, like reference numerals are assigned to them, and no explanation thereabout will be made for avoiding redundant repetition thereof.

Figure 7A:
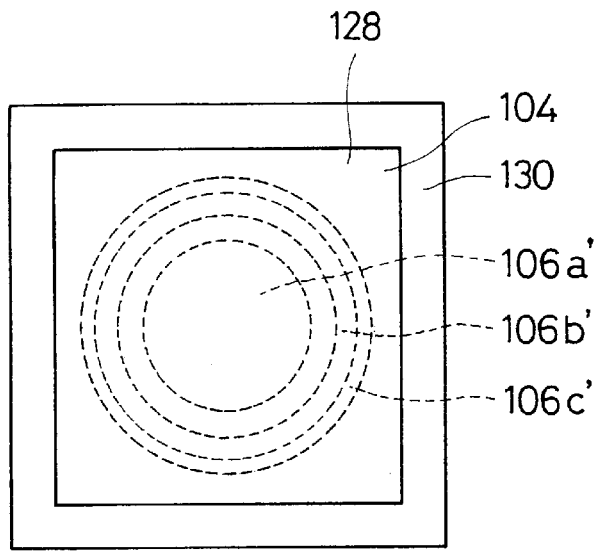
FIG. 7(A) is a perspective view for showing the relation between the base plate and the electrodes applicable to the third and fourth embodiments of the present invention.

The third embodiment is different from the first and second embodiments in the following point. Namely, instead of forming the first and second electrodes 106a and 106b on the surface 104a of a glass substrate 104, the first and second electrodes 106a', 106b' are disposed on the surface 128a of a base plate 128 arranged opposing to the surface 104a of the glass substrate 104. As shown in FIG. 7(A), the first electrode 106a' having an almost circular shape is formed almost at the center of the opposing surface 128a of the base plate 128 while the second electrode 106b' is prepared in the annular form coaxially surrounding the first electrode 106a'. Accordingly, if the opposing surface 128a of the base plate 128 is viewed from the glass substrate side, there will be seen such an electrode arrangement that is equivalent to what is shown in FIG. 2(A). The first and second electrodes are connected with the surface resistivity measuring device (not shown). In the same manner as in the first and second embodiments, an electrode 106c' of an almost circular shape is formed on the back surface 104b of the glass substrate 104 (see FIG. 2(B)).

A rod 128b is firmly fitted on the upper surface of the base plate 128 and is connected with a not shown driving mechanism, thereby enabling the base plate 128 to move back and forth with respect to the surface 104a of the glass substrate 104. In the first and second embodiment as explained in the above, the glass substrate 104 may be just placed in the isolated space 102 and it is not always necessary for the glass substrate to be at a specific fixed place within the isolated space. In the third embodiment, however, as will be described later, it is needed to bring the opposing surface 128a of the base plate 128 into contact with the surface 104a of the glass substrate 104 when measuring the surface resistivity, so that the glass substrate 104 has to be mounted on a stage 130 so as to receive a pushing force applied by the base plate.

Next, there will be explained about how to evaluate the atmosphere originated organic contamination over the substrate surface according to the third embodiment.

Figure 7B:
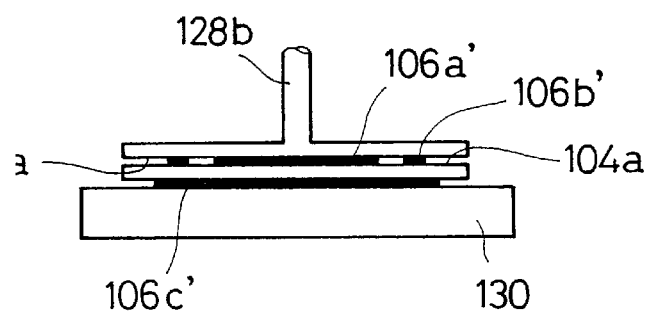
FIG. 7(B) is a diagrammatic representation showing the base plate getting in close contact with the electrodes applicable to the third and fourth embodiments of the present invention.
Figure 7C:
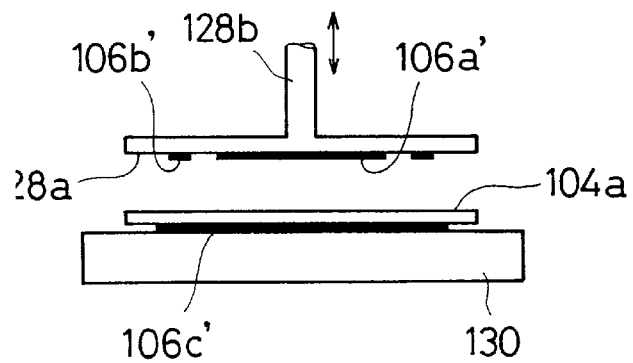
FIG. 7(C) is a diagrammatic representation showing the base plate separating from the electrodes applicable to the third and fourth embodiments of the present invention.

First, there is mounted on the stage 130 of the isolated space 102 the glass substrate 104 having the clean surface 104a that is made free from the organic substances by rinsing it. Then, valves V1, V4 are opened keeping valves V2 and V5 closed, and the pressurized humidity regulated gas of which the relative humidity is controlled to have a predetermined value by a humidifier 114 is supplied to the isolated space 102 through said humidifier. After the relative humidity in the isolated space has reached said predetermined value, the base plate 128 resting above the surface 104a of the glass substrate 104 (FIG. 7(C)) is moved downward to bring the first and second electrodes 106a', 106b' formed on its surface 128a into close contact with the opposing surface 104a of the glass substrate 104 (FIG. 7(B)). Then, the voltage is applied across the first and second electrodes 106a', 106b', thereby measuring the initial surface resistivity (Rsi) of the clean glass substrate by means of a not shown surface resistivity measuring device.

Next, the base plate 128 is moved upward to expose the surface 104a of the substrate 104 to the atmosphere of the isolated space 102, and at the same time, valves V1, V4 are closed while valves V3 and V6 are opened, and then, the objective atmosphere to be evaluated is sucked into the isolated space 102 by operating an air pump 122, thereby exposing the surface 104a of the glass substrate 104 to the objective atmosphere for a predetermined period of time. After completion of this exposure process, valves V3, V6 are closed while valves V1, V4 are opened. The relative humidity of the isolated space 102 is made to again return to the predetermined relative humidity (substantially equal to the relative humidity at which the surface resistivity of the substrate was measured immediately after rinsing it) with the help of the controller 124. Then, the base plate 128 is again moved downward to bring the first and second electrodes 106a' and 106b' into close contact with the surface 106 of the glass substrate 104. Then, the surface resistivity (Rsf) is measured by means of said not shown surface resistivity measuring device. In such a manner as described above, the change with passage of time in respect of the quantity of organic contaminants on the clean substrate surface can be pursued or monitored by repeating the measurement of the surface resistivity (Rsf) at regular intervals.

The isolated space 102 is provided with a UV lamp 126a installed on the side partition wall in the same manner as in the case of the second embodiment. After a series of measurements of the change with passage of time in respect of the surface resistivity is finished, valves V1, V4, V3, V6 are closed while valves V2, V5 are opened to supply the pressurized oxygen gas to the isolated space 102 from an oxygen cylinder 116. At the same time, the surface 104a of the substrate 104 is irradiated with UV rays from said UV lamp, thereby the organic contaminants deposited on the surface 104a being decomposed and removed through the so-called UV rays/ozone cleaning. After this UV rays/ozone cleaning, the valve V2 is closed while the valve V1 is opened keeping the valve V5 opened. Then, the inside of the isolated space 102 is made to replace with the purified air, exhausting the ozone gas generated in the isolated space 102 during said UV rays/ozone cleaning by operating an exhaust pump 120. In this way, the evaluation apparatus gets in the standby position for measurement of the change with passage of time in respect of surface resistivity of the next dean glass substrate.

Fourth Embodiment

Figure 8:
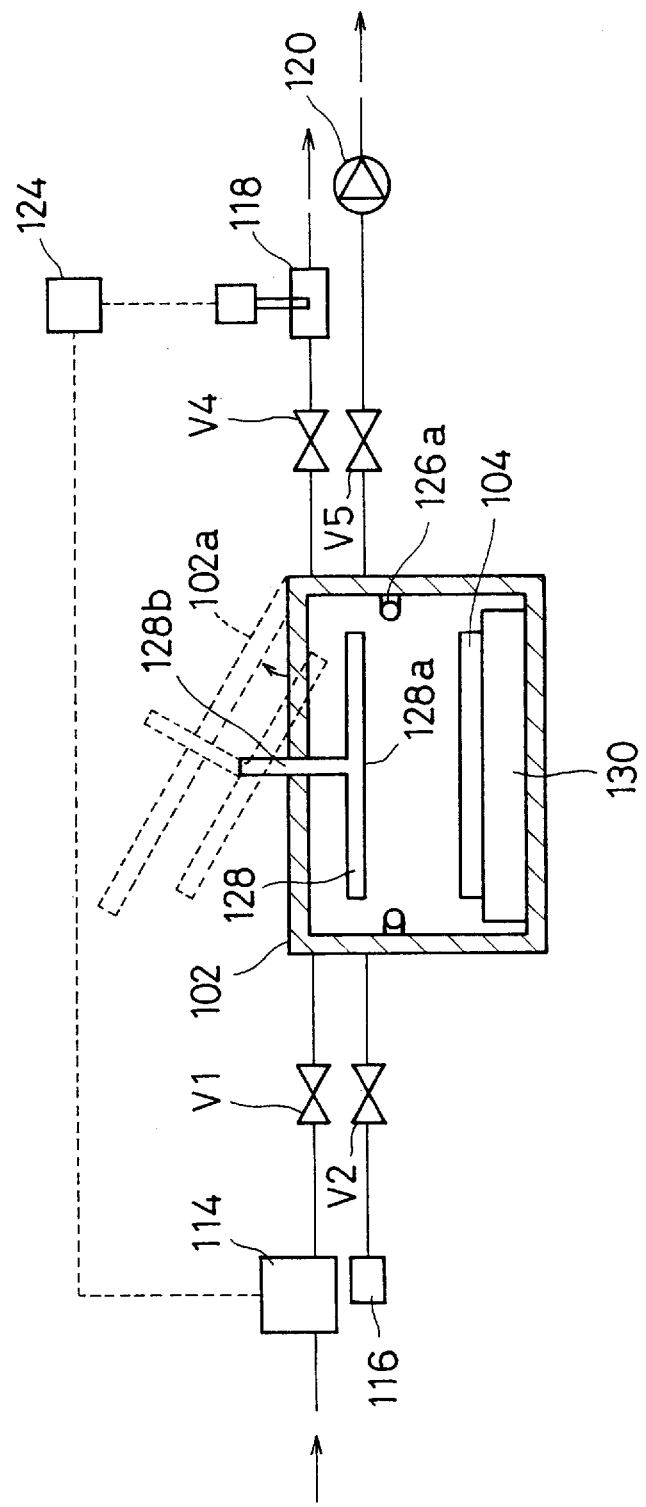
FIG. 8 is a schematic diagram showing the apparatus for evaluating the atmosphere originated organic contamination over the substrate surface according to the fourth preferred embodiment of the present invention.

Next, the fourth embodiment as shown in FIG. 8 will be described in the following. In this fourth embodiment, its constituents which perform the substantially same functions as those of the first through third embodiments, are given like reference numerals, and no explanation thereabout will be made for avoiding redundant repetition thereof. This fourth embodiment is achieved by applying the constitution of the third embodiment to the isolated space 102 having the openable door 102a as described in the second embodiment. Accordingly, in the same manner as in the case of the second embodiment, if the door 102a is opened, the atmosphere surrounding the isolated space 102 can naturally flow into the isolated space to fill up its inside therewith. Therefore, to be different from the third embodiment, there disappear the valves V3, V6 and the exhaust pump 122 of the third embodiment. A UV lamps 126a is disposed on the side portion of the isolated space not so as to disturb the opening and shutting movement of the door 102a.

Next, there will be explained about how to evaluate the atmosphere originated organic contamination over the substrate surface according to the fourth embodiment.

First, there is mounted on the stage 130 located in the isolated space 102 the glass substrate 104 having the clean surface 104a which is made free from the organic substances by rinsing. Then, valves V1, V4 are opened keeping valves V2, V5 closed, and the pressurized humidity regulated gas which is controlled so as to have a predetermined relative humidity by a humidifier 114, is supplied to the isolated space 102 through said humidifier. After the humidity inside the isolated space has reached said predetermined relative humidity, a base plate 128 is moved downward to bring the first and second electrodes 106a' and 106b' into close contact with the surface 104a of the glass substrate 104. Then, the voltage is applied across the first and second electrodes 106a' and 106b', thereby measuring the initial surface resistivity (Rsi) of the clean glass substrate by means of a not shown surface resistivity measuring device.

Next, the base plate 128 is lifted upward to expose the surface 104a of the substrate 104 to the atmosphere in the isolated space 102 and at the same time, valves V1 and V4 are closed while the door 102a is opened to fill up the isolated space 102 with the objective atmosphere to be evaluated, thereby exposing the surface 104a of the glass substrate 104 to the objective atmosphere for a predetermined period of time. After completion of this exposure process, the door 102a is closed while valves V1 and V4 are opened. The relative humidity of the isolated space 102 is made to again return to the predetermined relative humidity (substantially equal to the relative humidity at which the surface resistivity of the substrate was measured immediately after rinsing it). Then, the base plate 128 is again moved downward to bring the first and second electrodes 106a' and 106b' into close contact with the surface 104a of the glass substrate 104. Then, the voltage is applied across the electrodes, and the surface resistivity (Rsf) of the substrate 104 having been exposed to the objective atmosphere is measured by means of a not shown surface resistivity measuring device.

In the same manner as described in the preceding embodiments, the change with passage of time in respect of the quantity of organic contaminants on the clean substrate surface can be pursued or monitored by repeating the measurement of the surface resistivity (Rsf) at regular intervals. The isolated space 102 is provided with the UV lamp 126a like the preceding embodiments. After a series of measurements of the change with passage of time in the surface resistivity are finished and the base plate 128 is lifted up, valves V1, V4 and the door 102a are closed while valves V2 and V5 are opened so as to supply the pressurized oxygen to the isolated space 102 from an oxygen cylinder 116. At the same time, the surface 104a of the substrate 104 is irradiated with UV rays, thereby the organic contaminants deposited on the surface 104a being decomposed and removed by means of the so-called UV rays/ozone cleaning. At this time, in the same way as in the case of the preceding embodiments, the ozone gas generated in the isolated space is exhausted by an exhaust pump 120. In this way, the evaluation apparatus comes to stand ready to measuring the change with passage of time in respect of the surface resistivity of the next clean glass substrate.

Fifth Embodiment

Figure 9:
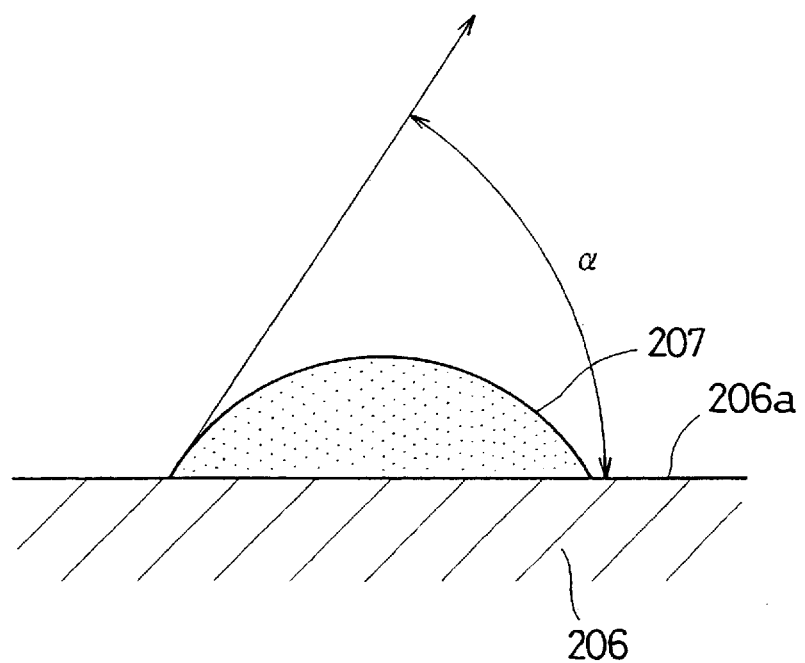
FIG. 9 is an illustration for explaining the relation between the liquid-drop and the contact angle in connection with the fifth and sixth embodiments of the present invention.
Figure 10:
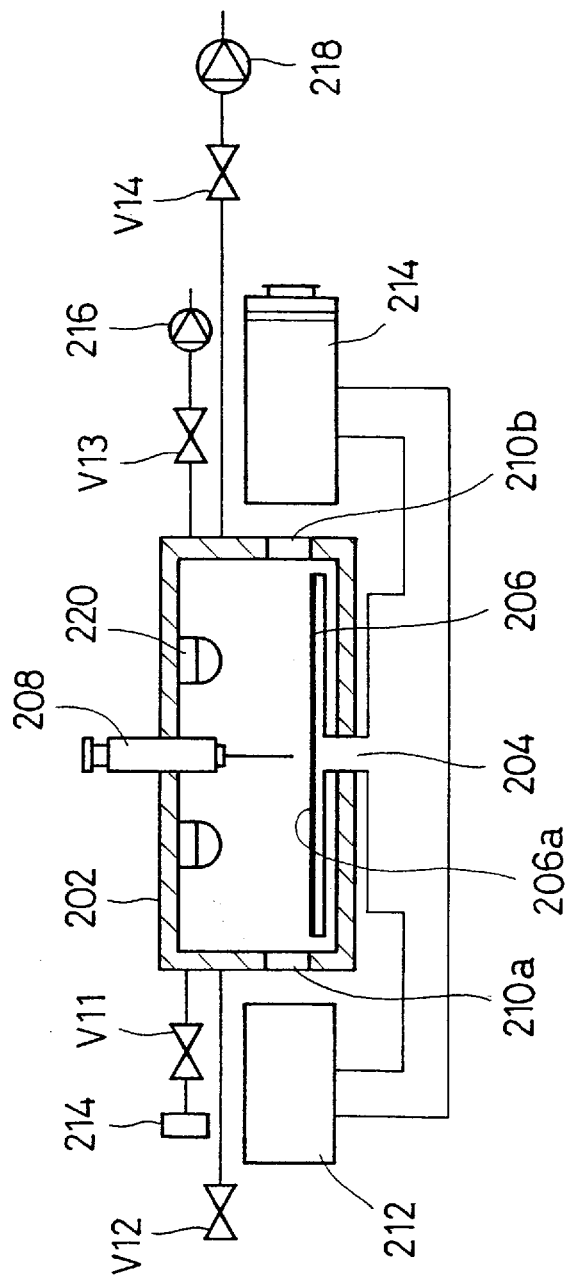
FIG. 10 is a schematic diagram showing the apparatus for evaluating the atmosphere originated organic contamination over the substrate surface according to the fifth preferred embodiment of the present invention.

Next, there will be explained referring to FIG. 10 the method and apparatus for evaluating the atmosphere originated organic contamination over the substrate surface according to the fifth embodiment of the present invention. The apparatus is provided with an isolated space 202 as in the preceding embodiments. This isolated space 202 can be constituted as a chamber which is isolated from the atmosphere surrounding it by means of partitions made of such a material as aluminum, for instance. In this isolated space 202, there is provided a stage 204 for receiving on it a glass substrate 206 having a clean glass surface 206a from which organic substances have been removed. Above the glass substrate 206, there is provided a syringe 208 for dropping an ultra-pure waterdrop 207 shown in FIG. 9 on the glass surface 206a. The stage 204 is associated with a transfer mechanism (not shown) capable of making the stage 204 rotate and/or parallelly transfer in a horizontal plane, so that there can be varied the dropping point of the waterdrop 207 dropped from the syringe 208 to the glass substrate 206.

Further, a pair of opposing partitions of the isolated space 202 are provided with observation window 210a, 210b by one each. On the outside of one observation window 210a, there is provided a light source 212 for illuminating the waterdrop 207 dropped on the glass substrate 206 while on the outside of the other observation window 210b, there is provided means for enlarging an image 214, for instance a microscope or a magnifying glass for observing and measuring the image of the waterdrop by enlarging it. Accordingly, a contact angle a of the waterdrop on the substrate surface can be measured by illuminating the waterdrop 207 dropped on the substrate 206 and observing it with the help of the magnifying glass 214.

It is made possible to introduce into the isolated space 202 a cleaning gas containing at least oxygen supplied from a cylinder 214 through a gas supply valve V11 and also the objective atmosphere to be evaluated can be introduced into the isolated space through a gas supply valve V12. The isolated space 202 is further connected with an exhaust valve V13 communicating with an exhaust pump 216 for exhausting the cleaning gas, and still further connected with an exhaust valve V14 communicating with an air pump 218 for exhausting the objective atmosphere. Also, there is provided on the upper portion of the isolated space 202 a UV 220 for irradiating the surface 206a of the glass substrate 206 with UV rays at the time of rinsing the substrate.

Next, there will be explained about how to evaluate the atmosphere originated organic contamination over the substrate surface by means of the evaluation apparatus as described above.

First, as to the clean substrate immediately after rinsing it, the measurement of the contact angle is carried out by using the magnifying glass 214. After this, valves V11, V13 are closed while valves V12, V14 are opened, thereby introducing the objective atmosphere into the isolated space 202 by operating the air pump 218. Then, after exposing the surface 206a of the substrate 206 to the objective atmosphere for a predetermined period of time and measuring the contact angle of the waterdrop at that time, the stage 204 is driven to transfer the substrate 206 mounted thereon in a horizontal plane. As described above, the present embodiment is constituted in such a manner that the stage 204 is driven, but it may be constituted in such a manner that the syringe 208 can be transfer in a horizontal plane keeping the substrate 206 (stage 204) standing still. In short, when there is finished the measurement of the contact angle about one waterdrop dropped at one dropping point on the substrate surface, the stage 204 or the syringe 208 is turned or horizontally transferred to receive another waterdrop at another dropping point on the substrate surface that has never received any waterdrop so far, and then, the next measurement of the contact angle is carried out about another waterdrop. In this manner, if the measurement of the contact angle is repeated at regular intervals, there can be pursued or monitored the change with passage of time in respect of the quantity of organic contaminants on the substrate surface.

After a series of measurements of the change with passage of time in respect of the contact angle are finished, valves V12, V14 are closed while valves V11, V13 are opened in order to introduce the cleaning gas containing at least oxygen supplied from the cylinder 214 into the isolated space 202. Further, the surface 206a of the substrate 206 is irradiated with UV rays from the UV lamp 220, thereby the organic contaminants deposited on the surface 206a being decomposed and removed by means of the so-called UV rays/ozone cleaning. After this UV rays/ozone cleaning, the valve 11 is closed while the valve 12 is opened keeping the valve V13 opened for expelling the ozone gas generated in the isolated space 202 at the time of cleaning thereof in order to replace it with the objective atmosphere. In this way, the evaluation apparatus comes to be stand ready to measure the change with passage of time with regard to the contact angle of the waterdrop dropped on the next clean glass substrate.

Figure 11:
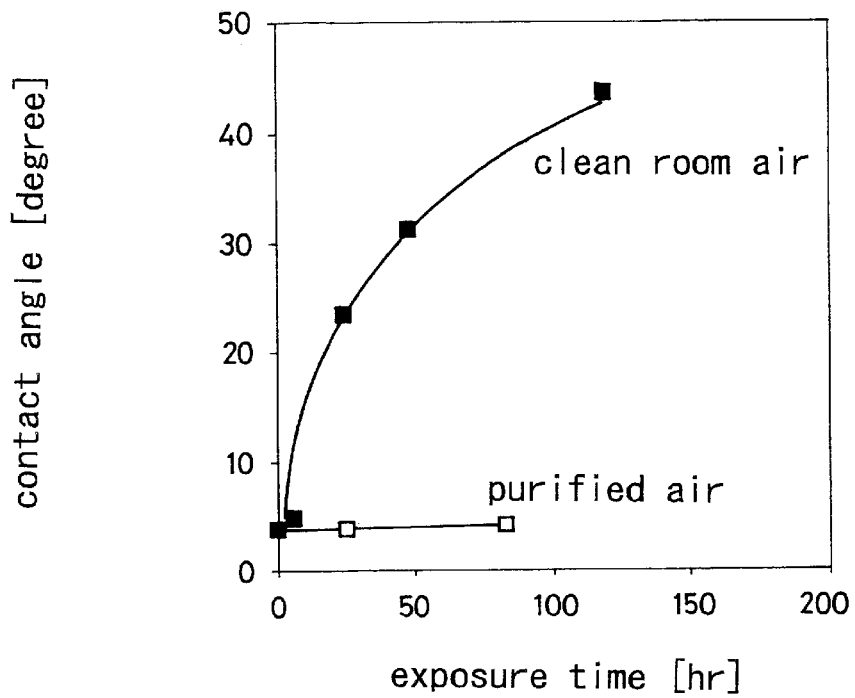
FIG. 11 is a graph showing the relation of the increasing rate of contact angle to the time of exposing the glass substrate surface to the specific atmosphere.
Figure 12:
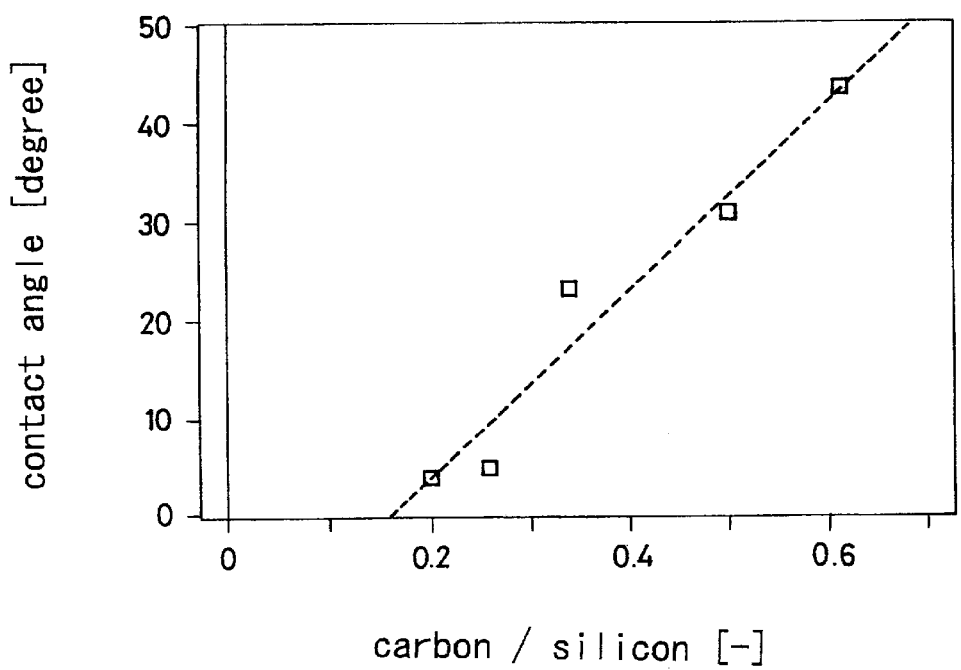
FIG. 12 is a graph showing the relation of the increasing rate of contact angle to the quantity of organic substances (ratio of carbon/silicon) adhered to the glass substrate surface.

FIG. 11 is a graph showing the relation between the time of exposing the substrate to the objective atmosphere and the contact angle, which has been obtained through the measurements of the contact angle. In these measurements, the glass substrates (CORNING #7059, 100×100 mm$^2$×1.1 mm$^t$) were used as sampling substrates while the clean room air and the purified air (resulting from removing the organic contaminants from the clean room air) were used as the objective atmosphere to be evaluated. As will been seen from the graph, in case of exposing the glass substrate to the clean room air, the contact angle increases with passage of exposure time. On the other hand, in case of exposing the same to the purified air, the contact angle is hardly increased. FIG. 12 is a graph showing relation between the contact angle and the organic contaminant quantity (carbon/silicon) deposited on said CORNING glass substrate, which has been measured by the XPS method. As shown in this graph, the contact angle increases corresponding to the increase in the quantity of organic contaminants deposited on the glass substrate (carbon /silicon), so that if the relation of FIG. 12 is made use of, it becomes possible to convert the measured value of the contact angle increasing rate into the quantity of the organic contaminants deposited on the glass substrate surface. For instance, if the glass substrate is exposed one by one to different objective atmospheres for a predetermined period of time and then the increasing rate of the contact angle is measured, it can be known from the results of respective measurements how much they contribute to contamination of the substrate surface as the sources thereof. Also, if the identical glass substrate is kept in a specific atmosphere and its contact angle is repeatedly measured at regular intervals, it can be continuously monitored whether the atmosphere originated organic contamination against the glass substrate surface is kept below the allowable level or not.

Sixth Embodiment

Figure 13:
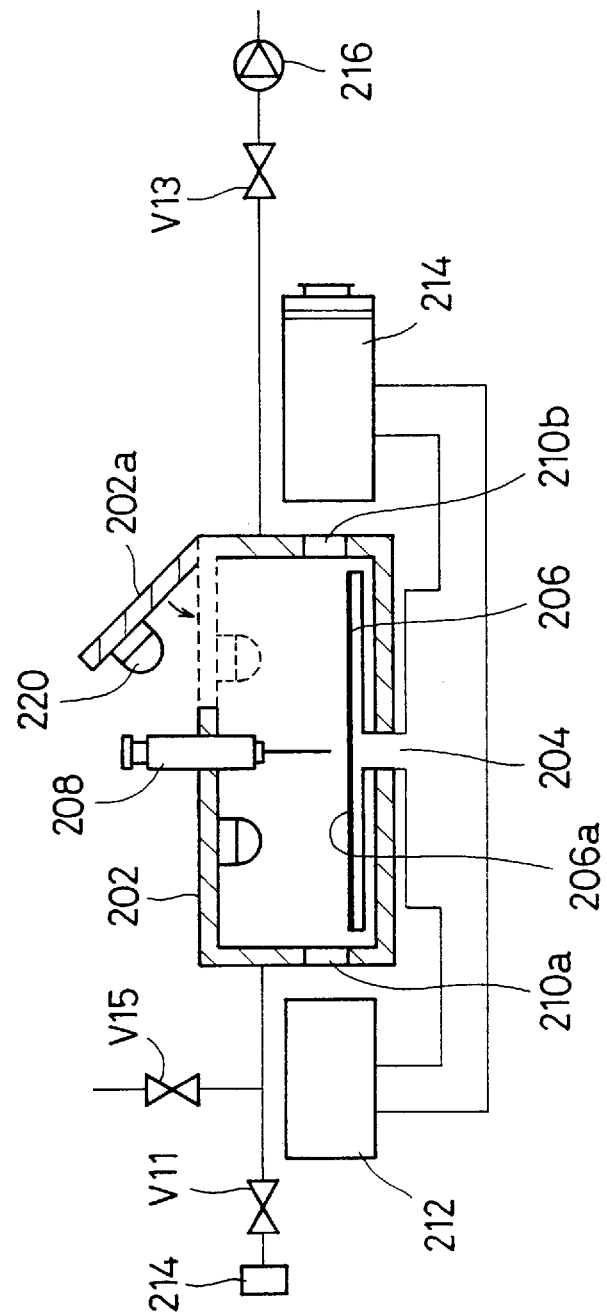
FIG. 13 is a schematic diagram showing the apparatus for evaluating the atmosphere originated organic contamination over the substrate surface according to the sixth preferred embodiment of the present invention.

The sixth embodiment of the invention will now be described in detail in the following. FIG. 13 is a schematic constitutional view of the apparatus for evaluating the atmosphere originated organic contamination over substrate surface contamination. With regard to the constituents of the sixth embodiment shown in FIG. 13, which perform the substantially same functions as those of the fifth embodiment shown in FIG. 10, like reference numerals are assigned thereto, and no explanation thereabout will be made for avoiding redundant repetition thereof.

The sixth embodiment is different from the fifth embodiment shown in FIG. 10 in the following point. Namely, the sixth embodiment is constituted in such a manner that the partition for separating the isolated space 202 from the atmosphere surrounding it is provided with an openable door 202$a$, so that the atmosphere can naturally flow into the isolated space 202 to fill it up therewith when the door 202$a$ is opened. In connection with provision of this door 202$a$, valves V12, V14 and the exhaust pump 218 are removed while a bypass valve V15 is added for introducing the atmosphere into the isolated space 202. In the fifth embodiment, the objective atmosphere to be evaluated is compulsively supplied to the isolated space 202, so that the objective atmosphere may exist remote from the site at which the isolated space 202 is located. For instance, the air in the storage room or chamber of materials like silicon wafers and LCD glass substrates, can be introduced into the isolated space, if providing the piping connecting therebetween. Contrary to this, according to the sixth embodiment, the objective atmosphere to be evaluated has to be the atmosphere surrounding the isolated space. For instance, this is the case that the objective atmosphere is the atmosphere of the clean room.

Next, there will be explained about how to evaluate the atmosphere originated organic contamination over substrate surface according to the sixth embodiment.

First, a substrate 206 is mounted on a stage 204 arranged in the isolated space 202 isolated from the atmosphere surrounding it, the surface 206$a$ of said substrate being made free from organic substances by cleaning. A syringe 208 is provided above the glass substrate 206 in order to drop an ultra-pure waterdrop 207 on the surface 206$a$ of the glass substrate 206. The stage 204 is associated with a transfer mechanism (not shown) capable of making the stage 204 rotate and/or parallelly transfer in a horizontal plane, in order to vary the dropping point of the waterdrop 207 to be dropped out of the syringe. First, a waterdrop 207 is dropped on the surface 206$a$ of the glass substrate 206 immediately after rinsing and then, the contact angle ($\alpha$) is measured by a magnifying glass 214, illuminating the waterdrop with the light from a lighting source 212. After the measurement of the contact angle, the door 202$a$ is opened, thereby the isolated space 202 being naturally filled up with the objective atmosphere. The change with passage of time in regard to the quantity of the organic contaminants deposited on the glass substrate can be pursued or monitored by repeating the measurement of the contact angle ($\alpha$) at regular intervals. The isolated space 202 is provided with the UV lamp 220, so that after completing a series of measurements of the change with passage of time in regard to the contact angle, the door 202$a$ is closed while valves V11, V13 are opened to introduce the cleaning gas containing at least oxygen supplied from the cylinder 214 into the isolated space 202. At the same time, the surface 206$a$ of the substrate 206 is irradiated with UV rays, thereby the organic contaminants deposited on the surface being decomposed and removed by means of the so-called UV rays/ozone cleaning. After this UV rays/ozone cleaning, the valve 11 is closed while the bypass valve 15 is opened keeping the valve V13 opened for expelling the ozone gas generated in the isolated space 202 at the time of cleaning thereof by operating the exhausting pump 216, replacing the ozone gas with the objective atmosphere. In this way, the evaluation apparatus enters in the state standing ready for the measurement of the change with passage of time in respect of the contact angle of the waterdrop dropped on the next clean glass substrate.

According to the present invention as explained in the above in connection with several embodiments thereof, the degree of the atmosphere originated organic contamination over a substrate made of silicon, glass, and so forth, can be evaluated by measuring the change with passage of time in respect of the surface resistivity of the insulating surface of the substrate, or by measuring the change with passage of time in regard to the contact angle of the waterdrop dropped on the surface of the substrate. Namely, according to the present invention, by evaluating the increasing quantity of the surface resistivity or the contact angle as to the substrate surface after being exposed to the clean room atmosphere in view of the initial value thereof as measured using the clean substrate surface immediately after rinsing it, it becomes possible to judge the allowable exposure period of time beyond which the atmosphere originated organic contamination exceeds a certain limit, in other words, the so-called maximum allowable exposure time indicative of the time limit that the substrate is able to stand against the exposure to the clean room atmosphere without inviting any irreparable damage.

Especially, in the manufacturing process of semiconductor devices and LCD products, the clean substrate surface immediately after having been treated in one film formation process by sputtering or plasma CVD, can not but be exposed to the clean room atmosphere while it is transferred to the other film formation process. Accordingly, if there can be known by the present invention the maximum allowable exposure time for which the clean substrate is allowed to be exposed to the clean room atmosphere, the following countermeasures may be taken: 1) trying to transfer the clean substrate to the next film formation process within the maximum allowable exposure time, 2) in case the substrate happens to be exposed to the clean room atmosphere exceeding the maximum allowable exposure time, trying to rinse it again, and 3) in case the progress of the production is impeded with too short maximum allowable exposure time as determined for the time, trying to extend the maximum allowable exposure time by filtering the organic contaminants in the clean room atmosphere with an active carbon filter or the like to lower the concentration of airborne contaminants or organic substances.

Needless to say, the present invention is not limited to the preferable embodiments as described above, and it is understood that variations and modifications may be made by anyone skilled in the art within the scope of technological concept as recited in the attached claims for patent, but as a matter of course, those should belong to the technological scope according to the present invention.

For instance, in the above preferable embodiments, the invention is described in connection with the case where the glass substrate is used for the purpose of sampling the atmosphere originated organic contaminants. Needless to say, however, it is possible to use various types of substrates other than the glass substrate as a sampling substrate, for instance a silicon wafer or the others that are actually used in the production process. In case of evaluating the atmosphere originated organic contamination based on the change in the surface resistivity, the surface of the sampling substrate has to be dielectric, but it is not always necessary for the substrate surface to be dielectric in case of using the contact angle for evaluation of the contamination, thus the invention being applicable to the sampling substrate having a conductive surface.

Furthermore, the isolated space may be the space that is just isolated from the atmosphere surrounding it, so that it is of course possible to constitute the isolated space apart from the production line set up in the clean room in such a manner that the objective clean room atmosphere can be introduced into the isolated space through the piping connecting it with the clean room, or to dispose the isolated space having an openable door directly in the clean room to introduce the objective clean room atmosphere thereinto through the openable door.

Although the ultraviolet lamp is installed inside the isolated space in the above embodiments, it is possible to dispose it outside the isolated space and to irradiate the substrate with ultraviolet rays by means of a suitable optical system.

Furthermore, as to the surface resistivity measuring device and the contact angle measuring device, only an example is described in the above. Accordingly, it is understood that variations and modifications may be made by anyone skilled in the art without departing from the gist of the present invention.

As has been discussed above, according to the present invention, the atmosphere originated organic contamination on the semiconductor substrate, the glass substrate, and so forth, can be readily evaluated by using commercial and economical measurement instrument like the surface resistivity measuring device and the contact angle measuring device.

Further, according to the present invention, the contamination by organic substances can be evaluated at the same place as the sampling substrate exposed to the objective atmosphere is collected, so that the degree of the atmosphere originated organic contamination is judged just at the production site of the semiconductor substrate or the glass substrate, thus it being possible to constitute an evaluation system suitable for the in-line analysis.

Still further, according to the present invention, by properly carrying out the evaluation of the atmosphere originated organic contamination over the substrate surface, it becomes possible not only to enhance the throughput in the production process by reducing the number of unnecessary process of rinsing the substrate, but also to increase the production yield by rinsing the substrate upon need and/or by removing organic substances from the atmosphere by filtration.

What is claimed is:

1. Apparatus for evaluating atmosphere originated organic contamination over a substrate surface comprising a substrate, at least the surface of which is dielectric; a surface resistivity measuring device for measuring an electric resistance between at least two points on said substrate surface; an isolated space for accommodating said substrate; means for introducing a humidity regulated gas into said isolated space, said humidity regulated gas having a substantially constant relative humidity; means for introducing an objective atmosphere to be evaluated into said isolated space; and means for evaluating the atmosphere originated organic contamination over the substrate surface in correspondence with the surface resistivity as measured by said surface resistivity measuring device.

2. Apparatus as claimed in claim 1 wherein said surface resistivity measuring device includes a plurality of conductive electrodes which are formed so as to closely get in contact with the dielectric surface of said substrate.

3. Apparatus as claimed in claim 1 wherein said surface resistivity measuring device includes a plurality of conductive electrodes which are movably formed so as to get in contact with and move away from the dielectric surface of said substrate.

4. Apparatus as claimed in claim 1 wherein there are provided means for generating ultraviolet rays by which said substrate accommodated in said isolated space can be irradiated, and means for introducing a cleaning gas containing at least oxygen into said isolated space.

5. Apparatus as claimed in claim 1 wherein said humidity regulated gas is an inert gas and/or purified air.

6. A method for evaluating atmosphere originated organic contamination over a substrate surface comprising the steps of:

introducing a first humidity regulated gas having a predetermined relative humidity into an isolated space accommodating a substrate, at least the surface of which is dielectric, and measuring a surface resistivity between at least two points on said substrate surface;

introducing an objective atmosphere to be evaluated into said isolated space, thereby exposing said substrate to said objective atmosphere for a predetermined period of time;

introducing a second humidity regulated gas having substantially the same relative humidity as said predetermined relative humidity into said isolated space, and measuring a surface resistivity between at least two points on said substrate surface having been exposed to the objective atmosphere; and evaluating the atmosphere originated organic contamination over the substrate surface in correspondence with a change in the surface resistivity as measured.

7. A method as claimed in claim 6 wherein said first and second humidity regulated gases are inert gases and/or purified air.

8. A method as claimed in claim 6 further comprising the step of introducing into said isolated space a cleaning gas containing at least oxygen after finishing evaluation of the atmosphere originated organic contamination and at the same time, irradiating said substrate surface with ultraviolet rays.

9. A method as claimed in claim 6 further comprising the step of purging any gas existed in said isolated space during the preceding step, prior to the steps of introducing said first humidity regulated gas, said second humidity regulated gas and said objective atmosphere into said isolated space.

* * * * *